United States Patent [19]

O'Reilly et al.

[11] Patent Number: 5,596,104
[45] Date of Patent: Jan. 21, 1997

[54] PREPARATION OF 3,4,6-TRIFLUOROPHTHALIC ACID

[75] Inventors: Neil J. O'Reilly, Grand Island; William S. Derwin, Buffalo; Henry C. Lin, Grand Island; Deanne M. Nowak, Schenectady, all of N.Y.

[73] Assignee: Occidental Chemical Corporation, Niagara Falls, N.Y.

[21] Appl. No.: 77,750

[22] Filed: Jun. 18, 1993

Related U.S. Application Data

[63] Continuation-in-part of Ser. No. 653,554, Feb. 11, 1991, abandoned, and Ser. No. 847,620, Mar. 4, 1992, abandoned, which is a continuation of Ser. No. 509,929, Apr. 16, 1990, abandoned, said Ser. No. 653,554, is a division of Ser. No. 315,746, Feb. 27, 1989, Pat. No. 5,047,553.

[51] Int. Cl.$^6$ ............................................. C07D 209/48
[52] U.S. Cl. ............................................. 548/480; 562/483
[58] Field of Search ............................... 548/473, 480; 562/480, 483

[56] References Cited

U.S. PATENT DOCUMENTS

| | | | |
|---|---|---|---|
| 4,374,266 | 2/1983 | Fifolt et al. | 562/456 |
| 4,374,267 | 2/1983 | Fifolt et al. | 562/456 |
| 4,769,493 | 9/1988 | Ito et al. | 562/480 |

FOREIGN PATENT DOCUMENTS 2750661  11/1977  Germany.

OTHER PUBLICATIONS

CA 105: 235968 (1995).
Bergmann et al, J.Chem. Soc., 1194 (1964).
Odinov et al, Zh. org. Khim. (1967), 37, 176.
Islam et al, Indian J. Chem., 16B, Jul. 1978, pp. 593–596.

*Primary Examiner*—Amelia Owens

[57] ABSTRACT

3,4,6-trifluorophthalic acid is prepared in high yield by reaction of a 3,4,6-trichloro-N-substituted phthalimide with potassium fluoride at temperatures in the range of 200° to 270° C. in the absence of a catalyst to form the corresponding trifluoro-N-substituted phthalimide which, in turn, is hydrolyzed to form the 3,4,6-trifluorophthalic acid.

21 Claims, No Drawings

PREPARATION OF 3,4,6-TRIFLUOROPHTHALIC ACID

This application is a continuation-in-part of U.S. application Ser. No. 07/653,554 filed Feb. 11, 1991 now abandoned (a division of U.S. application Ser. No. 07/315,746, filed Feb. 27, 1989 now U.S. Pat. No. 5,047,553), and a continuation-in-part of U.S. application Ser. No. 07/847,620 filed Mar. 4, 1992 now abandoned (a continuation of U.S. application Ser. No. 07/509,929, filed Apr. 16, 1990 now abandoned). This invention is directed to a method for the preparation of 3,4,6-trifluorophthalic acid. The product is a useful intermediate for the further preparation of 2,4,5-trifluorobenzoic acid which, in turn, is a useful chemical intermediate for the further preparation of such diverse products as liquid crystals and quinolone anti-bacterial agents.

BACKGROUND OF THE INVENTION

It is known that some fluorophthalic anhydrides or acids may be prepared by halogen exchange, that is, fluorination of the corresponding chlorinated phthalic anhydrides. However, success in this approach has varied depending on the degree of halogen substitution on the chlorophthalic anhydride reactant. Thus, 3-chlorophthalic anhydride, 4,5-dichlorophthalic anhydride, and 3,6-dichlorophthalic anhydride have all been reported in the literature to yield the corresponding fluorinated anhydrides upon reaction with potassium fluoride. (Fifolt, M. J. and Foster, A. M., U.S. Pat. Nos. 4,374,266 and 4,374,267; and Bergman, E. D., Bentov, M., and Levy, A. J. Chem. Soc. (1964) 1194). However, under similar conditions, attempts at direct fluorination of higher chlorinated anhydrides have been reported as unsuccessful. Odinokov, V. N., Yakobson, G. G., and Vorozhtsov, Jr. N. N. Zh. Org. Khim. (1967), 37, 176, disclose that the reaction of tetrachlorophthalic anhydride with potassium fluoride in dimethylformamide produced no tetrafluorophthalic anhydride with octafluoroanthraquinone as the only identified product. A similar reaction in the absence of a solvent was reported by the same investigators to yield 40–45% octafluoroanthraquinone. Furthermore, the present inventors have attempted direct fluorination of trichlorophthalic anhydride by reaction with potassium fluoride under varying conditions with extremely low yields (less than 10%).

Ito, H., Matsuschita, U., Shimizu, T., and Ishikowa, N. (U.S. Pat. No. 4,769,493) disclose the preparation of N-substituted tetrafluorophthalimide by reaction of the corresponding N-substituted tetrachlorophthalimide.

Islam, A. M., El-Sharief, A. M. S. and Bedair, A. H. (Indian J. Chem., 16B, July 1978, p. 593–596), disclose the preparation of N-phenyl-triiodophthalimide by reaction of triiodobenzalphthalide with hydrazine hydrate.

It is an object of the present invention to provide a novel and efficient process for the preparation of 3,4,6-trifluorophthalic acid.

SUMMARY OF THE INVENTION

It has now been found that 3,4,6-trifluorophthalic acid may be prepared in high yield by reacting 3,4,6-trichloro-N-substituted phthalimide with potassium fluoride at temperatures in the range of 200° to 270° Celsius, in the absence of a catalyst to form the corresponding trifluoro-N-substituted phthalimide which, in turn, is hydrolyzed to form the 3,4,6-trifluorophthalic acid.

The trichloro-N-substituted phthalimides suitable for use in the process of the present invention include compounds characterized by the formula:

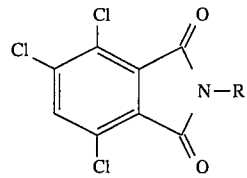

wherein R is a monovalent organic group derived from a primary amine of the formula $RNH_2$. The starting phthalimide reactant is conveniently prepared by the reaction of 3,4,6-trichlorophthalic anhydride with a primary amine of the formula $RNH_2$ wherein the R corresponds to the R of the phthalimide (I) and is selected from the group consisting of $C_{1-12}$ alkyl, phenyl, $C_{1-12}$ monoalkylphenyl, naphthyl, and $C_{1-12}$ monoalkylnaphthyl.

DETAILED DESCRIPTION OF THE INVENTION

The fluorination reaction of the present process, that is, the reaction between 3,4,6-trichloro-N-substituted phthalimide with potassium fluoride is preferably carried out in the presence of a solvent. The reaction may be run neat, however, this approach is not preferred. Suitable solvents include, for example, non-polar solvents, such as dichlorobenzene, xylene, trichlorobenzene, or the like; or preferably, polar, aprotic solvents, such as, sulfolane, dimethylsulfoxide, N-methylpyrrolidone, acetonitrile, dimethylsulfone, dimethylformamide, or dimethylacetamide. The preferred solvent, based on efficiency of reaction and minimization of production of solvent-related by-products, is sulfolane.

The high conversions achieved in the fluorination reaction of the present invention, typically 90% or higher conversion, in a relatively short period of time, such as less than about two hours, is achieved when the process is carried out at temperatures in the range of about 200° to about 270° Celsius. At lower temperatures the percent conversion is substantially diminished. Temperatures above about 270° Celsius may be employed, but are generally unnecessary. Preferably the reaction is carried out at a temperature in the range of about 220° to about 260° Celsius. It is a specific advantage of the present invention that the fluorination reaction may be carried out in the absence of a catalyst, thereby eliminating the need for subsequent separation of the catalyst from the product and disposal or recycling of the catalyst. Not only is the lack of need for a catalyst advantageous, but it is particularly surprising to find that the fluorination reaction of the present process may be carried out in the absence of a catalyst with substantial improvements in yield.

It is a further advantage of the present process that the large excess of potassium fluoride traditionally used in fluorination exchange reactions, is unnecessary. It has been found that no more than a 20% stoichiometric excess of potassium fluoride is required and, in fact, it has been found that in some instances, the use of larger excesses may lead to a deterioration of the reaction.

The hydrolysis step, that is the formation of 3,4,6-trifluorophthalic acid from the 3,4,6-trifluoro-N-substituted phthalimide may be carried out in a typical fashion in the presence of an aqueous acid, typically at temperatures ranging from about 80° to reflux, depending on the acid strength. Typically the hydrolysis of the N-substituted phthalimide is carried out in 25 to 89% aqueous sulfuric acid.

To further illustrate the present invention and the manner in which it may be practiced the following specific examples are set forth:

EXAMPLES 1 and 2

Preparation of Phthalimide Reactants

Example 1

3,4,6-Trichloro-N-phenylphthalimide 3,4,6-Trichlorophthalic acid (500 g, 1.86 moles), glacial acetic acid (4 L), and aniline (175 mL, 1.92 moles) were charged to a 12 L 3-neck flask equipped with a condenser, a stirrer and a thermometer. The mixture was heated with stirring and maintained at 100°–101° C. for 2 hours, then cooled to room temperature and filtered. The filter cake was washed with cold water and vacuum dried (70° C., 0.2 mmHg) for 24 hours to yield 590.7 g of 97.5% pure 3,4,6-trichloro-N-phenylphthalimide (m.p. 199°–200° C.).

Example 2

3,4,6-Trichloro-N-methylphthalimide

A mixture of 3,4,6-trichlorophthalic acid (25.01 g, 92.8 mmol) and glacial acetic acid (100 mL) was charged to a 250 mL 3-neck flask, equipped with a dry-ice condenser, thermometer, gas sparger and magnetic stirrer and maintained under an atmosphere of dry nitrogen. The mixture was heated and maintained at 50°–54° C. while methylamine (12 g, 0.4 mol) was introduced over a period of 1.5 hours. Following the addition of the methylamine, the reaction mixture was heated to 93° C. and maintained thereat for about 5 hours, then cooled to room temperature and filtered. The filter cake was washed with cold water and vacuum dried (0.2 mmHg) for 24 hours to yield 15.97 g of 3,4,6-trichloro-N-methylphthalimide as a white powder (m.p. 166°–167.5° C.).

EXAMPLES 3–4

Preparation of 3,4,6-Trifluoro-N-substituted Phthalimides

Example 3

Preparation of 3,4,6-Trifluoro-N-phenylphthalimide 3,4,6-Trichloro-N-phenylphthalimide (10.0 g, 30.1 mmol), potassium fluoride (6.45 g, 111.0 mmol) and sulfolane (100 mL) were charged to a 250 mL round-bottom flask equipped with a condenser and magnetic stirrer, maintained under a nitrogen atmosphere. The reaction mixture was heated, with stirring, at a bath temperature of 235°–243° C. for a period of 70 minutes. The mixture was then cooled and filtered. The filter cake was washed with methylene chloride and the wash combined with the filtrate. Sulfolane was removed by distillation and toluene (50 mL) added to the residue. After filtering to remove some insoluble material (0.40 g), the solution was introduced at the top of a silica column and eluted with toluene. Removal of the solvent from the fractions containing the product, followed by vacuum drying (0.2 mmHg, 16 h) gave 3,4,6-Trifluoro-N-phenylphthalimide as a cream colored solid (57.4 g, 20.7 mmol, mp 183°–185° C., 91% pure by G.C. area %), a yield of 67.6%.

Example 4

Preparation of 3,4,6-trifluoro-N-methylphthalimide

Following the general procedure of Example 3, 3,4,6-trichloro-N-methylphthalimide (9.82 g, 37.12 mmol) was reacted with potassium fluoride (7.77 g 133.7 mmol) in sulfolane (100 mL) at a temperature of 240° C. over a period of 1.1 hours. Analysis of the reaction product by $^{19}$F NMR, using 4-fluoronitrobenzene as an internal standard, indicated an 83.2% yield.

EXAMPLE 5

Hydrolysis of 3,4,6-Trifluoro-N-phenylphthalimide

A 1L 3-neck flask, equipped with a condenser, thermometer, and mechanical stirrer, was charged with 3,4,6-trifluoro-N-phenylphthalimide (45.76 g, 140.1 mmol, 72% pure by G. C. internal standard v. hexadecane) and 25% sulfuric acid (600 mL). The reaction mixture was heated, with stirring, to 105° C. and maintained thereat for 27.8 hours, then cooled to room temperature and filtered. The filter cake was washed with water twice and the filtrate extracted four times with ethyl acetate. The combined extracts were dried over anhydrous magnesium sulfate, filtered, and the solvent removed on a rotary evaporator. The remaining solid was vacuum-dried at 0.2 mmHg for 24 hours to 29.79 g (81.5% yield) of 3,4,6-trifluorophthalic acid as an off-white solid (mp 153°–155° C., purity 91.8% by G. C. area %).

EXAMPLE 6

Hydrolysis of 3,4,6-Trifluoro-N-methylphthalimide

Following the procedure of Example 5, 3,4,6-trifluoro-N-methylphthalimide (0.5087 g, 2.4 mmol) was hydrolyzed in 25% sulfuric acid (10 mL, 125° C., 29 h) to give 0.4721 g of 3,4,6-trifluorophthalic acid as a white solid (mp 154°–156° C.).

The following examples illustrate the catalyzed fluorination of 3,4,6-trichloro-N-phenylphthalimide (Ex. 7C) and 3,4,6-trichloro-N-methylphthalimide (Ex. 8C) and are provided for purposes of comparison.

EXAMPLE 7C

Catalyzed Fluorination of 3,4,6-Trichloro-N-phenylphthalimide

A 25 mL round-bottom flask equipped with a magnetic stirrer and a condenser was charged with 3,4,6-trichloro-N-phenylthalimide (1.01 g, 3.1 mmol), potassium fluoride (0.61 g, 10.5 mmol), tetraphenylphosphonium bromide (0.10 g) and sulfolane (10 mL) under a dry-nitrogen atmosphere. The reaction mixture was then heated with stirring at a bath temperature of 140° C. (24 h), then cooled and filtered. The filter cake was washed twice with methylene chloride. The filtrate was concentrated on a rotary evaporator and 4-fluoronitrobenzene (0.1005 g) was added as a $^{19}$F NMR internal standard. NMR analysis showed the yield of 3,4,6-trifluoro-N-phenylphthalimide to be 44.1%.

EXAMPLE 8C

Catalyzed Fluorination of 3,4,6-Trichloro-N-methylphthalimide

The procedure of Example 7C was repeated except that in place of the 3,4,6-trichloro-N-phenylphthalimide there was substituted 1.0 g of 3,4,6-trichloro-N-methylphthalimide and 9.2 molar equivalents of potassium fluoride and the reaction was run for 32.1 hours. Analysis of the reaction product by NMR analysis indicated a yield of 46.9% of 3,4,6-trifluoro-N-methylphthalimide.

The non-catalyzed fluorination, following the general procedure of Examples 3 and 4, was repeated using various conditions. For comparative purposes, the catalyzed fluorination, following the general procedure of Examples 7C and 8C was repeated using various catalysts and conditions.

The ranges of conditions and results achieved are set forth below.

Non-Catalyzed Flourination

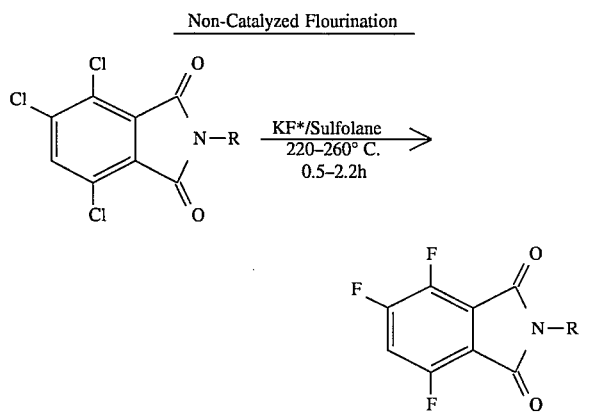

*3–20% excess KF used

Yield (by $^{19}$F NMR, internal standard)
R=Phenyl 53–66%
R=Methyl 63–83%

Catalyzed Flourination

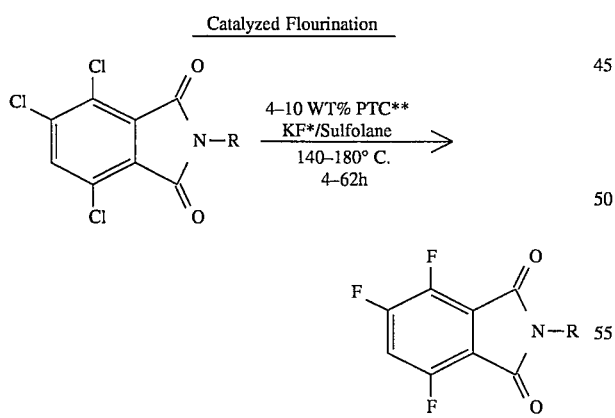

*10–370% excess KF used
** various catalysts employed included:
 tetraphenylphosphonium bromide,
 tetraphenylphosphonium chloride, and
 tributylhexadecylphosphonuim bromide Yield (by $^{19}$F NMR, internal standard)
R=Phenyl 29–47%
R=Methyl 21–57%

What is claimed is:

1. A process for the preparation of 3,4,6-trifluorophthalic acid which comprises
   A) reacting potassium fluoride with 3,4,6-trichloro-N-R-phthalimide at a temperature of about 200° to 270° Celsius under anhydrous conditions and in the absence of a catalyst to form 3,4,6-trifluoro-N-R-phthalimide wherein R is the same in each instance and is selected from the group consisting of $C_{1-12}$ alkyl, phenyl, $C_{1-12}$ monoalkyl phenyl, naphthyl and $C_{1-12}$ monoalkyl naphthyl, and
   B) hydrolyzing the 3,4,6-trifluoro-N-R-phthalimide to form 3,4,6-trifluorophthalic acid.

2. A process according to claim 1 carried out in the presence of a solvent.
3. A process according to claim 2 carried out in the presence of a polar aprotic solvent.
4. A process according to claim 3 carried out at a temperature of about 220° to 260° Celsius.
5. A process according to claim 1 wherein R is phenyl.
6. A process according to claim 5 carried out at a temperature of about 220° to 260° Celsius.
7. A process according to claim 6 wherein the solvent is sulfolane.
8. A process according to claim 1 wherein R is methyl.
9. A process according to claim 8 carried out at a temperature of about 220° to 260° Celsius.
10. A process according to claim 9 wherein the solvent is sulfolane.
11. A process for the preparation of a trifluorophthalimide of the formula

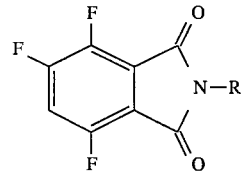

wherein R is selected from the group consisting of $C_{1-12}$ alkyl, $C_{1-12}$ monoalkyl phenyl, naphthyl and $C_{1-12}$ monoalkyl naphthyl, which comprises reacting potassium fluoride with a trichlorophthalimide of the formula

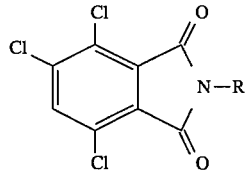

wherein R is as defined above, the process being carried out at a temperature of about 200° to 270° Celsius in the absence of a catalyst.

12. A process according to claim 11 carried out in the presence of a solvent.
13. A process according to claim 12 carried out in the presence of a polar aprotic solvent.
14. A process according to claim 13 for the preparation of 3,4,6-trifluoro-N-phenylphthalimide which comprises reacting potassium fluoride with 3,4,6-trichloro-N-phenylphthalimide.
15. A process according to claim 14 carried out at a temperature of about 220° to 260° Celsius.
16. A process according to claim 15 wherein the solvent is sulfolane.

17. A process according to claim 13 for the preparation of 3,4,6-trifluoro-N-methylphthalimide which comprises reacting potassium fluoride with 3,4,6-trichloro-N-methylphthalimide.

18. A process according to claim 17 carried out a temperature of about 220° C. to 260° C.

19. A process according to claim 18 wherein the solvent is sulfolane.

20. 3,4,6-Trifluoro-N-phenylphthalimide.

21. 3,4,6-Trifluoro-N-methylphthalimide.

* * * * *